(12) United States Patent
Anderson

(10) Patent No.: US 8,203,020 B2
(45) Date of Patent: Jun. 19, 2012

(54) METHOD OF ISOLATING SHIKIMIC ACID FROM A PLANT

(75) Inventor: Kim A. Anderson, Corvallis, OR (US)

(73) Assignee: Kim A. Anderson, Corvallis, OR (US)

( * ) Notice: Subject to any disclaimer, the term of this patent is extended or adjusted under 35 U.S.C. 154(b) by 0 days.

(21) Appl. No.: 11/897,970

(22) Filed: Aug. 30, 2007

(65) Prior Publication Data

US 2008/0058210 A1     Mar. 6, 2008

Related U.S. Application Data

(60) Provisional application No. 60/841,643, filed on Aug. 30, 2006.

(51) Int. Cl.
*C07C 61/00*        (2006.01)
(52) U.S. Cl. ........................................................ 562/510
(58) Field of Classification Search .................. None
See application file for complete search history.

(56) References Cited

U.S. PATENT DOCUMENTS

| | | |
|---|---|---|
| 6,436,664 B1 | 8/2002 | Iomantas et al. |
| 6,613,552 B1 | 9/2003 | Frost et al. |
| 6,794,164 B2 | 9/2004 | Malmberg et al. |
| 2003/0138920 A1 | 7/2003 | Malmberg et al. |

OTHER PUBLICATIONS

Pornpakakul et al. Tetrahedron letters 2000, 41, 2691-2694.*
Anderson et al. Communications in Soil Science and Plant Analysis, 2001, 32(17&18), 2831-2840.*
Breshnahan et al., J. Agric. Food Chem. 2003, 51, 4004-4007.*
Karpf et al., J. Org. Chem. 2001, 66, 2044-2051.*
Harring et al., T., Accumulation of Shikimic Acid: A Technique for Screening Glyphosate Efficacy, J. Agric. Food. Chem. 1998, 46, 4406-12.
Waters, Identifying and Quantitating Compounds, http://www.waters.com/waters/nav.htm?cid=10049055&locale=en_US.
Raghavendra, et al., Prospecting for Alternate Sources of Shikimic Acid, a Precursor of Tamiflu, a Bird-Flu Drug, Curr. Sci. (2009), 96, 771-72, available at http://www.ias.ac.in/currsci/mar252009/771.pdf.
ChaCha.com, How Tall Can Wheat Grow?, http://www.chacha.com/question/how-tall-can-wheat-grow.
eHow.com, How to Grow Alfalfa, http://www.ehow.com/how_2386126_grow-alfalfa.ht.
University of Minnesota, Growth and Development Guide for spring Wheat, http://www.extension.umn.edu/distribution/cropsystems/dc2547.html.
Ott, Eric J., Weed Management in Illinois No-Till Wheat, available at http://www.illinoiswheat.org/EricOttWeedManagement-FINAL.ppt.
Yenish et al., Abstract of Effect of Preharvest Glyphosate Application on Seed and Seedling Quality of Spring Wheat (*Triticum aestivum*), Weed Tech. vol. 14, 212-17, http://www.jstor.org/pss/3988529.
U.S. Department of Agriculture, Glyphosate-Tolerant Alfalfa Events J101 and J163: Request for Nonregulated Status: Draft Environmental Impact Statement, p. 20 (Nov. 2009), available at http://www.aphis.usda.gov/biotechnology/downloads/alfalfa/gealfalfa_deis.pdf.
Waters, How Does High Performance Liquid Chromatography Work?, http://www.waters.com/waters/ nav.htm?cid=10049064&locale=en_US.

* cited by examiner

*Primary Examiner* — Yevegeny Valenrod
(74) *Attorney, Agent, or Firm* — Marger Johnson & McCollom, P.C.

(57) ABSTRACT

The present invention provides a method of isolating shikimic acid from a plant. First, a plant is provided. Next, the plant is grown in the absence of glyphosate for a first time period. The plant is then treated with glyphosate for a second time period. This second time period is sufficient for the glyphosate to increase the amount of shikimic acid in the plant. The plant with increased amounts of shikimic acid is then harvested and the shikimic acid is isolated from the plant.

14 Claims, 2 Drawing Sheets

METHOD OF ISOLATING SHIKIMIC ACID FROM A PLANT

CROSS-REFERENCE TO RELATED APPLICATIONS

This application claims the benefit of U.S. Application No. 60/841,643, filed Aug. 30, 2006, which is incorporated herein by reference.

FIELD OF THE INVENTION

The present invention relates generally to chemistry. More particularly, the present invention relates to methods of producing and isolating shikimic acid from a plant.

BACKGROUND

In the pharmaceutical industry, shikimic acid from chinese star anise is used as a base material for production of Tamiflu (oseltamivir). In early 2005, Roche announced a production shortage of oseltamivir. According to Roche, the major bottleneck in oseltamivir production is the availability of shikimic acid, which cannot be synthesised economically and is only effectively isolated from Chinese star anise, an ancient cooking spice. The low isolation yield of shikimic acid from chinese star anise is blamed for the 2005 shortage of oseltamivir. Star anise is grown in four provinces in China and harvested between March and May. It is also produced in Lang Son province, Vietnam. The shikimic acid is extracted from the seeds in a ten-stage manufacturing process. Thirteen grams of star anise make 1.3 grams of shikimic acid, which can be made into 10 oseltamivir 75 mg capsules. Ninety percent of the harvest is already used by Roche in making oseltamivir.

Although most autotrophic organisms produce shikimic acid, it is a biosynthetic intermediate and generally found in very low concentrations. Shikimic acid can also be extracted from the seeds of the sweetgum fruit, which is abundant in North America, in yields of around 1.5%, so just 4 kg of sweetgum seeds are enough for fourteen packages of Tamiflu. By comparison star anise has been reported to yield 3 to 7% shikimic acid. Recently biosynthetic pathways in *E. coli* have been enhanced to allow the organism to accumulate enough material to be used commercially. Other potential sources of shikimic acid include the ginkgo tree. However, current extraction procedures for shikimic acid are typically labor and reagent intensive. Accordingly, there is a need in the art to develop new sources of and new extraction procedures for shikimic acid.

SUMMARY OF THE INVENTION

The present invention satisfies both of these needs. Specifically, the present invention provides a method of isolating shikimic acid from a plant. First, a plant is provided. Next, the plant is grown in the absence of glyphosate for a first time period. The plant is then treated with glyphosate for a second time period. This second time period is sufficient for the glyphosate to increase the amount of shikimic acid in the plant. The plant with increased amounts of shikimic acid is then harvested and the shikimic acid is isolated from the plant.

Shikimic acid may be isolated from any plant according to the present invention. Preferably, the plant is an agricultural crop plant, such that the method may be performed simultaneously on a plurality of plants. Also preferably, the plant may be grown and harvested several times in a year such that the method can be repeated at least one per year. Examples of such plants include, but are not limited to, alfalfa and wheat. Preferably, the plant is treated with a sublethal amount of glyphosate.

Shikimic acid may be isolated from a glyphosate-treated plant by any means according to the present invention. Preferably, a water extraction method is used. Liquid chromatography may also be used for increased purity of product.

BRIEF DESCRIPTION OF THE FIGURES

The present invention together with its objectives and advantages will be understood by reading the following description in conjunction with the drawings, in which.

DETAILED DESCRIPTION OF THE INVENTION

Figure 1:
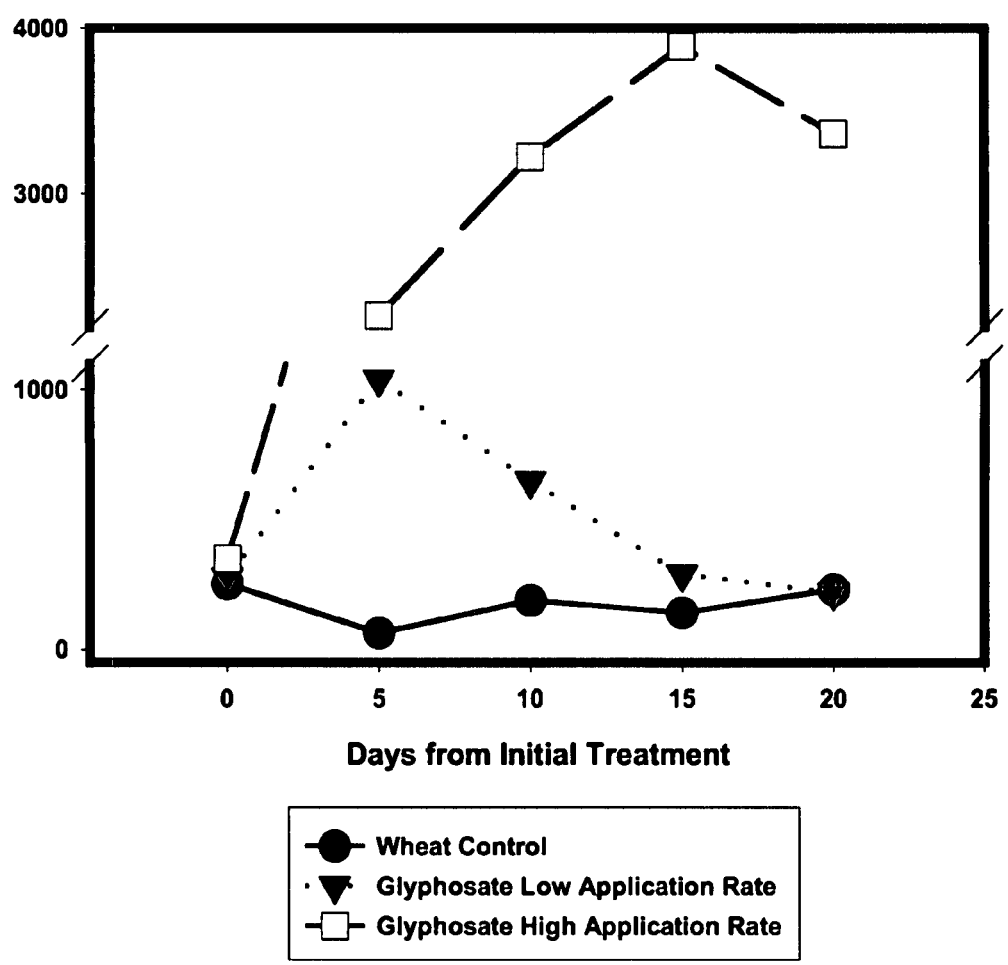
FIG. 1 shows an example of a chromatogram of shikimic acid isolated according to the present invention.

According to the present method, a plant is provided. Any plant that is sensitive to glyphosate may be used according to the present invention. As hundreds of plants are sensitive to glyphosate, the present method is widely applicable. In one embodiment, the plant is an agricultural crop, including but not limited to alfalfa and wheat. Preferably, the plant matures rapidly and can be grown several times in one year. Also preferably, many of the same plant can be grown simultaneously, such that the method can be performed on all plants at the same time.

The plant is then grown for a first period of time in the absence of glyphosate. The exact time period will depend on the specific plant, and is a balance between obtaining shikimic acid quickly and obtaining a high yield of shikimic acid. In addition, plant maturity for ease of harvesting must be taken into account. In a large-scale setting, the plants should be grown until they are between about 8" and about 10" tall. In a greenhouse setting, plants can be much smaller. The first time period is flexible and dependent on weather conditions. In one embodiment, the first time period is between about four and six weeks. The plant is grown under conditions that are typical for the plant of choice.

Next, the plant is treated with glyphosate for a second period of time. At the biochemical level, the primary mode of glyphosate action is inhibition of the enzyme 5-enolpyruvlyshikimiate-3-phosphate synthase. This results in the blockage of the shikimate pathway causing a reduction in aromatic amino acid synthesis, reduced protein synthesis, reduced growth and premature cellular death. Typically a plant shuttles about 20-25% of its total photosynthate carbon through the shikimate pathway. Blockage of the shikimate pathway results in accumulation of high levels of shikimic acid. Glyphosate blockage of the shikimate pathway effectively short-circuits any feedback mechanism in the pathway. Consequently, the plant puts even more carbon into the pathway in an effort to overcome the lack of biosynthetic products, hence further hastening or intensifying injury or death. Thus, normally, glyphosate is used to kill unwanted plants such as weeds. According to the inventive method, however, plants are deliberately exposed to glyphosate in order to raise their shikimic acid levels. Thus, both the dose of glyphosate and the second time period must be carefully controlled to maximize the amount of shikimic acid that may eventually be harvested. In a preferred embodiment, the plants are subjected to a sublethal dose of glyphosate. Preferably, this dose is between about 10% and about 50% of the lethal dose of glyphosate for the specific plant. The time period can range from a few hours to many days. In one embodiment, the second time period is at least 4 days.

As the plants are still alive after glyphosate treatment, they may be harvested using traditional harvesting equipment. This is a huge advantage, as it maximizes time and efficiency of harvesting. Any harvesting equipment or means known in the art may be used to harvest the plants.

The shikimic acid may then be isolated from the glyphosate-treated plants using any means known in the art. Preferably, the isolation method is a water extraction method, such as the method described below. Further purification can be achieved using, for example, liquid chromatography.

EXAMPLES

Field Demonstration:

Field trial plots with glyphosate on Express spring wheat were established at three treatment levels, untreated control, 4 oz formulated/acre, and 14 oz formulated/acre. Field site studies were conducted in eastern Washington, near Kennewick, Wash. There were buffer zones around each treat level and control plot. The whole above ground plant was harvested at time zero, 5, 10, 15, and 20 days after application. The samples were cooled immediately and frozen within one hour. The samples were received from the field and stored in the freezer at <−10 C. At the time of application plants were 8-10 inches tall, after 20 days the control plants were 20-24 inches and beginning to head out.

The field trial samples were then analyzed to corroborate and illustrate the method of the present invention (FIG. 1). In the low treat rate (4 oz) samples, shikimic acid was found to be significantly elevated by the day-5 sampling, with shikimic acid a factor of 4 above normal. By day-10 shikimic acid was returning to normal levels, although still a factor of 2 above normal, and by day-15 the wheat shikimic acid levels were nearly within normal range. The day 20 samples had shikimic acid levels that were within normal levels.

The higher treat rate (14 oz) shikimic acid samples were found to be significantly elevated by day-5, a factor of 6 above normal shikimic acid levels. The shikimic acid level continued to increase, and day-10 shikimic acid levels were a factor of 10 above normal. The shikimic acid remains elevated through the study period of 20 days.

Shikimic acid begins to buildup in susceptible plants within hours of exposure, so harvesting the plant for shikimic acid may begin shortly after glyphosate application.

Shikimic Acid Extraction:

Plant tissue was placed in an open container and dried at ca. 70 C overnight (14 to 16 hrs). Each sample was ground to pass through a 20 mesh screen. The ground sample was placed in a glass jar. Sealed samples may be stored at $\leq-10$ C for several months (the longest time tested). Approximately 150 mg of dry ground sample weight was placed into a screw cap bottle, 30 mL of DI water was added, and the bottle was capped and placed on a shaker overnight (14 to 16 hrs) at a minimum of 50 rpm. Extracts were filtered through a Whatman GF/A filter. For quantification, an aliquot was filtered (0.45 µm disposable) into an HPLC auto-sampler vial.

HPLC analysis was performed on a Perkin-Elmer ISS 200. Instrument conditions were as follows: column 250×4.6 mm ALTEX Ultrasphere 5 µm ODS (or equivalent);mobile phase (isocratic) 50 mM $KH_2PO_4$ solution adjusted to pH 2.4; flow rate 2 mL/min, detector 214 nm. Calibration curves consisted of 1, 5, 10, 50, 100 and 200 µg/mL standards, $r^2$ values were $\geq 0.998$. Retention time was ca. 2.0 min.

The entire plant tissue extract can be scaled up to accommodate larger extraction batch sizes. The shikimic acid may be cleanly extracted as described above or further cleanup may be accomplished using a direct scaled-up version of the analytical LC method described here.

Figure 2:
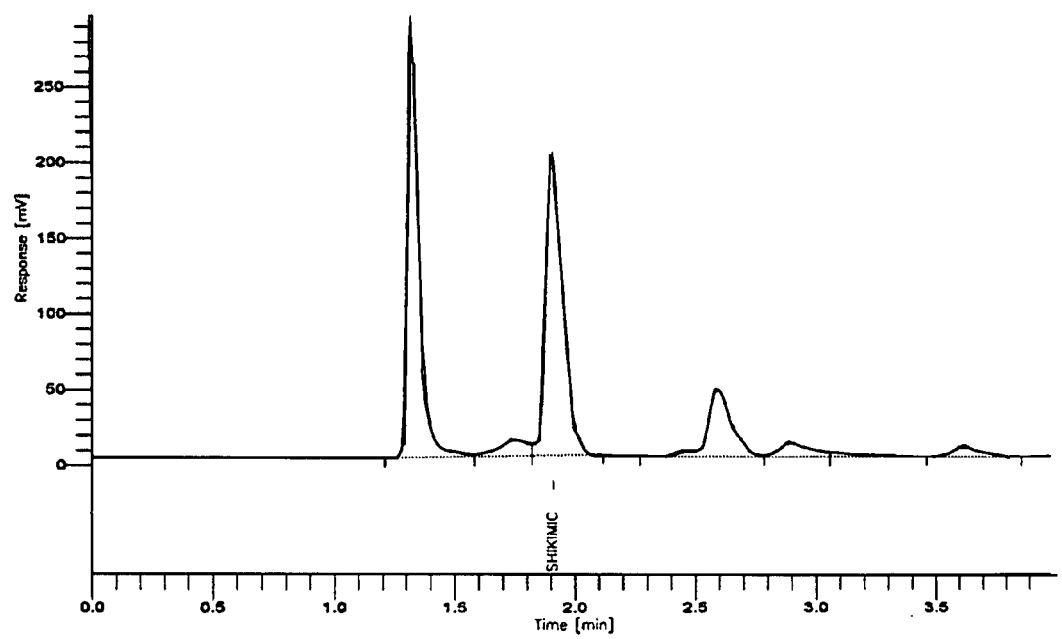
FIG. 2 shows an example of shikimic acid buildup in wheat using the method according to the present invention.

The water extraction used here gives excellent recoveries of shikimic acid, and provides for clean (interference free) chromatography, see FIG. 2. Shikimic acid elutes at ca. 2 min, total analysis time is less than 4 min. The HPLC method is isocratic, further simplifying the procedure. The process can be scaled via synthesis LC to generate the purified shikimic acid. Because of the clean extraction, quick elution of shikimic acid, and isocratic mobile phase, the entire analytical analysis can be performed quickly. A total of 15-16 samples/hour may be analyzed, an uncharacteristically high sample load for a chromatographic method.

The method provided here provides a technique to isolate shikimic acid from many types of plants including wheat, a relatively clean matrix. The method described here only takes 4-7 weeks to produce a crop with elevated levels of shikimic acid. This approach significantly reduces turn-around-time compared to the current bio-derived approaches such as star anise extracts. The method described is precise, accurate, and demonstrated good recoveries of shikimic acid in wheat plant tissues. No specialized or add-on equipment was required, a standard HPLC was used. The extraction technique adequately recovers shikimic acid, while providing for interference free clean extractions as demonstrated in the analytical chromatogram. The procedures are fully amenable to programmed operation and autosampling. Turnaround time is short and analyst interaction time is minimal. The method requires minimal sample, often a requirement in greenhouse studies. The method minimizes reagents and no organic solvents or strong acids/bases are used. The method minimizes waste, and greatly reduces toxic/hazardous chemicals compared to currently used methodology. The method adheres and qualifies as a green technique as outlined by the principles of green chemistry.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A method of obtaining purified shikimic acid in commercially usable amounts, comprising:
   providing an agricultural crop;
   growing the agricultural crop in the absence of glyphosate for a first time period;
   at the end of the first time period, deliberately exposing the agricultural crop to a sublethal dose of glyphosate sufficient to cause the agricultural crop to express shikimic acid at a level above normal;
   growing the agricultural crop for a second time period sufficient for the glyphosate to increase the shikimic acid in the agricultural crop to a commercially extractable amount; wherein the second time period is 10 days or less;
   at the end of the second time period, harvesting the agricultural crop;
   extracting the shikimic acid from the harvested agricultural crop; and
   purifying the extracted shikimic acid.

2. The method as set forth in claim 1, wherein the agricultural crop is alfalfa.

3. The method as set forth in claim 1, wherein the first time period ends at a time that is between about 4 weeks and 6 weeks from planting.

4. The method as set forth in claim 1, wherein the second time period is at least 4 days.

5. The method as set forth in claim 1, wherein the extracting comprises a water extraction method.

6. The method as set forth in claim 1, wherein the purifying comprises synthesis liquid chromatography.

7. The method as set forth in claim 1, further comprising repeating the method at least one time per year.

8. The method as set forth in claim 1, wherein the agricultural crop is wheat.

9. The method as set forth in claim 1, wherein the sublethal dose is between about 10% and 50% of a lethal dose of glyphosate for the agricultural crop.

10. The method of claim 1 further comprising using the purified shikimic acid to produce oseltamivir.

11. The method of claim 1 wherein the time at which the first time period ends is when the agricultural crop is between about 8" and 10" tall.

12. The method of claim 1 wherein the commercially extractable amount is an amount 1% dry weight or higher.

13. A method of obtaining purified shikimic acid from an agricultural crop comprising:

providing the agricultural crop;

growing the agricultural crop in the absence of glyphosate for a first time period that is approximately 4 to 6 weeks long;

at the end of the first time period, deliberately applying to the agricultural crop a sublethal dose of glyphosate sufficient to cause the agricultural crop to express shikimic acid at a level above normal;

growing the agricultural crop for a second time period sufficient for the glyphosate to increase the shikimic acid in the agricultural crop to an amount that is 1% dry weight or higher wherein the second time period is 10 days or less;

at the end of the second time period harvesting the agricultural crop;

extracting the shikimic acid from the harvested agricultural crop; and purifying the extracted shikimic acid.

14. The method of claim 12 wherein the time at which the first time period ends is when the agricultural crop is between about 8" and 10" tall.

* * * * *